United States Patent [19]
Henderson

[11] Patent Number: 5,976,505
[45] Date of Patent: Nov. 2, 1999

[54] METHOD FOR CRYOGENICALLY TREATING PSORIASIS WITH LIQUID NITROGEN OR LIQUID NITROUS OXIDE

[75] Inventor: R. Winn Henderson, Knoxville, Tenn.

[73] Assignee: HCS Trust, Knoxville, Tenn.

[21] Appl. No.: 08/887,032

[22] Filed: Jul. 2, 1997

[51] Int. Cl.⁶ ................................................ A61K 9/12
[52] U.S. Cl. .......................... 424/45; 514/887; 514/863
[58] Field of Search ............................... 424/45; 514/887, 514/863

[56] References Cited

U.S. PATENT DOCUMENTS 3,946,733  3/1976  Han .
4,787,135  11/1988  Blum et al. .
4,802,475  2/1989  Weshahy .
4,865,028  9/1989  Swart .

OTHER PUBLICATIONS

M.J. Stiller, M.D., A management update on psoriasis, Hospital Medicine, Jan., 1994, pp. 28–35.

Primary Examiner—Raj Bawa
Attorney, Agent, or Firm—Pitts & Brittian, P.C.

[57] ABSTRACT

A method of cryogenically treating psoriatic lesions. In accordance with the present method, a cryogenic agent is applied by the spray technique to the surface of a psoriatic lesion for a period of time sufficient to "frost" the psoriatic lesion with the duration stopping short of the time necessary to cause formation of a fluid bullae or sloughing off of the affected tissue.

4 Claims, 1 Drawing Sheet

METHOD FOR CRYOGENICALLY TREATING PSORIASIS WITH LIQUID NITROGEN OR LIQUID NITROUS OXIDE

TECHNICAL FIELD

This invention relates to the field of cryogenic treatment of skin lesions. More particularly, it relates to a method of cryogenically treating psoriasis.

BACKGROUND ART

Psoriasis is a common cutaneous disease, affecting approximately two percent of the U.S. population. Classic plaque like psoriasis is the most common form of the disease which most typically manifests itself in erythematous lesions with silvery scales on the elbows, knees, sacrum, buttocks and scalp. The degree of physical and psychological disability ranges from slight to devastating. And, while there are a number of treatments, including topical medications, phototherapy and internal medications, the literature states that psoriasis is incurable. See Stiller, M. J., A Management Update on Psoriasis, *Hospital Medicine*, January 1994, pp. 28–35.

In the art of treating certain types of skin lesions, warts, pre-cancerous and cancerous lesions, cryotherapy is a known treatment modality. However, cryotherapy has not previously been reported as a psoriasis treatment. Two main techniques for cryosurgery are reported in the literature. Namely, a spray technique (ST) in which cryogen is applied directly onto the target site and a cryoprobe technique (CP) in which the surface of a probe, (that has been previously cooled by the cryogen), is applied to the target site instead of the actual cryogen. The objective of state of the art cryogenic therapy is destruction of the tissue. This destruction is the result of freezing of the tissue and transformation of water within the tissue into biologically inert ice crystals. This leads to cessation of circulation in the tissues with intra- and extra-cellular biochemical, anatomical and physiological sequel the end of which is tissue anoxemia and ischemic necrosis. It is known that, as a result of this freezing, a bullae of fluid develops in the areas treated. Subsequently, the damaged tissue on top of the bullae separates and sloughs off and the new skin below the fluid becomes the new surface. In U.S. Pat. No. 4,802,475, issued to A. H. A. G. Weshahy on Feb. 7, 1989, a novel probe for applying intralesional cryotherapy with the CP technique and a method for using the same is described. Further, in U.S. Pat. No. 4,865,028, issued to W. J. B. Swart on Sep. 12, 1989, discloses a device for carrying out cryotherapy. Further patents for treating skin conditions include U.S. Pat. No. 3,946,733, issued to J. S. Han on Mar. 30, 1976, for a moxibustion apparatus and U.S. Pat. No. 4,784,135, issued to S. E. Blum on Nov. 15, 1988, for far ultraviolet surgical and dental procedures. What has been missing from the art is a method of cryogenically treating psoriasis, without causing tissue anoxemia and ischemic necrosis of the tissues below the lesion, and which substantially reduces the chance of recurrence of the psoriatic lesion in the same location.

Accordingly, it is an object of the present invention to provide a method of cryogenically treating psoriatic lesions.

Another object of the present invention is to provide a method of cryogenically treating psoriatic lesions which does not result in destruction of the underlying tissue layer.

Still another object of the present invention is to provide a method of cryogenically treating psoriasis which substantially decreases the chance of recurrence of the psoriatic lesion in the same localized area of a patient's body.

Other objects and advantages over the prior art will become apparent to those skilled in the art upon reading the detailed description as follows.

DISCLOSURE OF THE INVENTION

In accordance with the various features of this invention, a method of cryogenically treating psoriatic lesions is provided. In accordance with the present method, a cryogenic agent is applied by the spray technique to the surface of a psoriatic lesion for a period of time sufficient to "frost" the psoriatic lesion with the duration stopping short of the time necessary to transform the solute water in the underlying healthy tissue into biologically inert crystals. In the preferred embodiment, the frosting only involves the surface area and depth of the lesion and is not of sufficient depth or duration to cause formation of a fluid bullae or sloughing off of the affected tissue.

BRIEF DESCRIPTION OF THE DRAWINGS

FIG. 2 is a photograph of a psoriatic lesion prior to treatment with the method of the present invention.

FIG. 3 is a photograph of the same area after treatment with the method of the present invention.

BEST MODE FOR CARRYING OUT THE INVENTION

Figure 1:
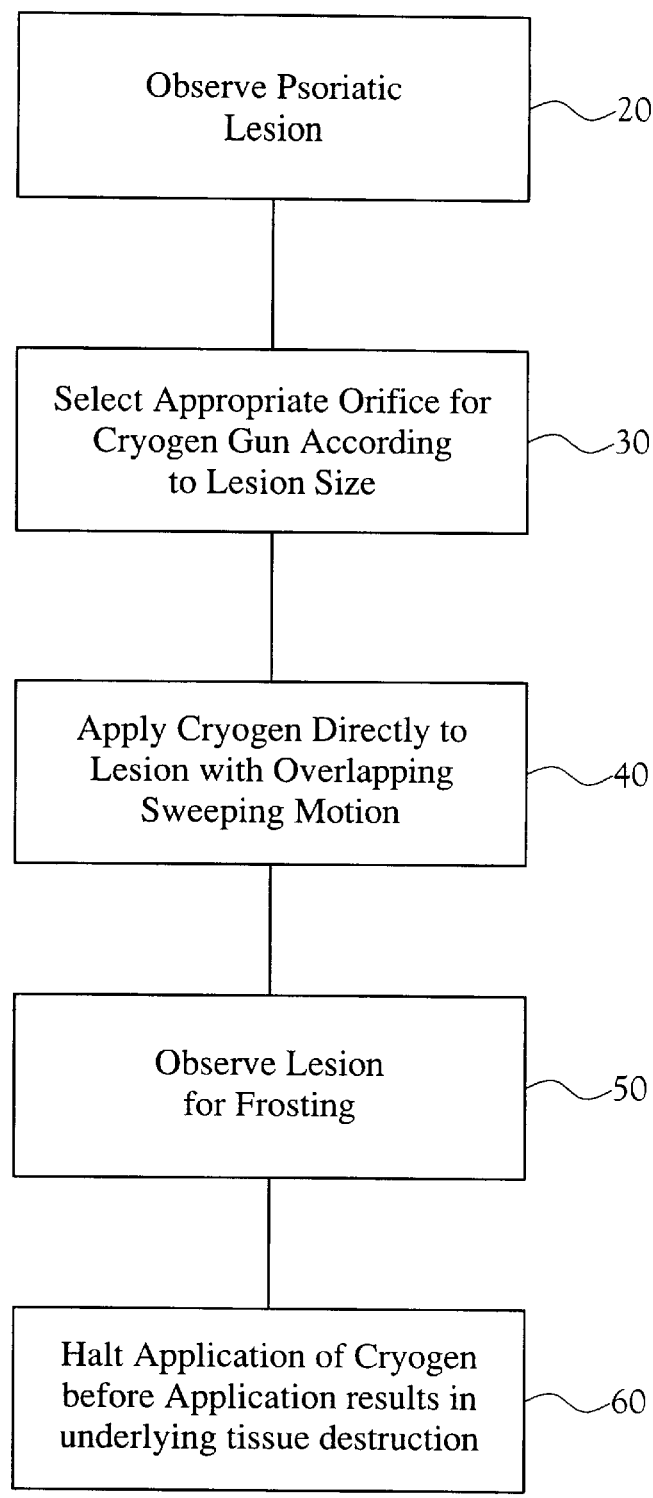
FIG. 1 illustrates a flow diagram showing the steps of the method of the present invention.

In the cryogenic treatment of psoriatic lesions in accordance with the present invention the attending medical person first observes the psoriatic lesion, as at 20 in FIG. 1. An untreated psoriatic lesion is illustrated at FIG. 2. A cryogenic agent, preferably liquid nitrogen, (L-$N_2$), is applied directly to the psoriatic lesion. Those skilled in the art will recognize that liquid nitrous oxide, (L-$N_2O$), is also a useable cryogen. However, those skilled in the art will appreciate that L-$N_2$ has a substantially lower boiling point than L-$N_2O$ and thus use of L-$N_2O$ will result in longer exposure to the cryogen and a higher attendant risk of freezing, and destroying, underlying healthy tissue.

While the cryogen can be applied topically by use of a swab, in the preferred embodiment the cryogen is applied by spraying. In this regard, a cryogen gun having an orifice tip of the appropriate width is used. The orifice tip is chosen depending upon the size of the psoriatic lesion as at 30. In the preferred method, the orifice tip emits a wide, flat spray of cryogenic agent. The cryogen is applied directly to the lesion in an overlapping, sweeping manner 40 with the desired effect being a cooling and "frosting" of the lesion with the depth of the frosting effect being no greater than the depth of the psoriatic lesion. The technician applies the cryogen for a length of time sufficient to observe the frosting of the lesion 50 without causing bullae formation and the attendant destruction of the underlying healthy tissue and the sloughing of the treated tissue. Thus, application of the cryogen is halted before destruction of the underlying tissue occurs 60. This shortened duration of treatment is sufficient to cause the psoriatic lesion to go into remission without destroying the underlying tissue. It is important that the time of exposure to the cryogenic agent does not result in cessation of circulation in the deeper tissues with the attendant intra- and extra-cellular biochemical, anatomical and physiological sequel that result in tissue anoxemia and ischemic necrosis. A psoriatic lesion that has been treated with the above method is illustrated at FIG. 3.
}

From the foregoing description, it will be recognized by those skilled in the art that a method of cryogenically treating psoriatic lesions offering advantages over the prior art is provided. Specifically, the method of the present invention provides a method of cryogenically treating psoriatic lesions which does not result in destruction of the underlying tissue layer and which substantially decreases the chance of recurrence of the psoriatic lesion in the same localized area of a patient's body.

While a preferred embodiment has been described, it will be understood that it is not intended to limit the disclosure, but rather it is intended to cover all modifications and alternate methods falling within the spirit and the scope of the invention as defined in the appended claims.

I claim:

1. A method of cryogenically treating a psoriatic lesion on a surface of skin wherein healthy tissue having solute water underlies said psoriatic lesion, said method comprising the steps:

applying a cryogenic agent selected from the group consisting of liquid nitrogen and liquid nitrous oxide directly to said psoriatic lesion wherein continued application of said cryogenic agent to said psoriatic lesion will sequentially result in a cooling of said psoriatic lesion, frosting of said psoriatic lesion and freezing of underlying healthy tissue;

observing said psoriatic lesion for said frosting;

halting said application of said cryogenic agent upon said observation of said frosting of said psoriatic lesion and prior to said freezing of underlying tissue, wherein said application of said cryogenic agent is halted prior to said freezing of said underlying healthy tissue thereby preventing destruction of said underlying healthy tissue.

2. The method of claim 1 wherein said cryogenic agent is applied by spraying.

3. The method of claim 2 wherein said cryogenic agent is sprayed from a cryogen gun.

4. A method of cryogenically treating a psoriatic lesion on a surface of skin wherein healthy tissue having solute water underlies said psoriatic lesion, said method comprising the steps:

applying a cryogenic agent selected from the group consisting of liquid nitrogen and liquid nitrous oxide directly to said psoriatic lesion with a cryogen gun having an orifice tip for emitting a wide, flat, spray of said cryogenic agent wherein continued application of said cryogenic agent to said psoriatic lesion will sequentially result in cooling of said psoriatic lesion, frosting of said psoriatic lesion, and freezing of underlying healthy tissue;

observing said psoriatic lesion for frosting;

halting said application of said cryogenic agent upon said observation of said frosting of said psoriatic lesion and prior to said freezing of said underlving healthy tissue, wherein said application of said crvogenic agent is halted prior to destruction of said underlying healthy tissue.

* * * * *